United States Patent
Belenkaya et al.

(10) Patent No.: US 8,183,427 B2
(45) Date of Patent: May 22, 2012

(54) BIODEGRADABLE ABSORBENTS AND METHODS OF PREPARATION

(76) Inventors: Bronislava G. Belenkaya, San Jose, CA (US); Valentina I. Sakharova, Moscow (RU); Vyacheslav N. Polevov, Moscow (RU); Claudia Polevov, legal representative, Moscow (RU)

(*) Notice: Subject to any disclaimer, the term of this patent is extended or adjusted under 35 U.S.C. 154(b) by 0 days.

(21) Appl. No.: 12/962,374

(22) Filed: Dec. 7, 2010

(65) Prior Publication Data
US 2011/0076250 A1 Mar. 31, 2011

Related U.S. Application Data

(63) Continuation of application No. 11/986,751, filed on Nov. 26, 2007, now Pat. No. 7,858,837, which is a continuation of application No. 10/267,823, filed on Oct. 9, 2002, now Pat. No. 7,309,498.

(60) Provisional application No. 60/328,454, filed on Oct. 10, 2001.

(51) Int. Cl.
*A61F 13/00* (2006.01)

(52) U.S. Cl. .......... 602/48; 424/443; 424/445; 424/447; 424/448; 424/449

(58) Field of Classification Search .............. 602/41–59; 424/443–445
See application file for complete search history.

(56) References Cited

U.S. PATENT DOCUMENTS
7,309,498 B2 * 12/2007 Belenkaya et al. .......... 424/443
2003/0069369 A1 * 4/2003 Belenkaya et al. .......... 525/437

FOREIGN PATENT DOCUMENTS
RU 2120306 C1 * 10/1998
* cited by examiner

*Primary Examiner* — Kim M Lewis

(57) ABSTRACT

A biodegradable microfiber absorbent comprises a substantially homogeneous mixture of at least one hydrophilic polymer and at least one biodegradable polymer. The absorbent can be prepared by an electro hydrodynamic spinning of a substantially homogeneous polymer mixture. Medical dressings for burns and wounds, cavity dressings, drug delivery patches, face masks, implants, drug carriers that comprises at least one microfiber electrospun from a polymer mixture are provided. The dressings can have variable water vapor penetration characteristics and variable biodegradation times.

23 Claims, 2 Drawing Sheets

BIODEGRADABLE ABSORBENTS AND METHODS OF PREPARATION

CROSS REFERENCE TO RELATED APPLICATIONS

The present application is a continuation application of, and claims priority to, U.S. patent application Ser. No. 11/986,751, entitled "Biodegradable absorbents and methods of preparation," filed Nov. 26, 2007 now U.S. Pat. No. 7,858,837, which is a continuation application of U.S. patent application, entitled "Biodegradable Absorbents and Methods of Preparation," Ser. No. 10/267,823, filed on Oct. 9, 2002, now U.S. Pat. No. 7,309,498, which claims priority to U.S. provisional patent application Ser. No. 60/328,454, filed on Oct. 10, 2001. The disclosures of these copending applications are hereby incorporated by reference herein. The present application claims priority of U.S. provisional patent application No. 60/328,454 filed on Oct. 10, 2001, incorporated herein by reference.

BACKGROUND OF THE INVENTION

The present invention relates to the field of biodegradable hydrophilic nonwoven absorbents and more particularly to microfiber biodegradable absorbents prepared by the electrohydrodynamic method from blends of synthetic biodegradable polyesters and poly (N-vinyl) lactams which can be used for a variety of applications including wounds and burns dressings, drug carriers and for cosmetic applications.

It has been known to use poly (N-vinyl) pyrrolidone (PVP) complexes with polyurethanes to yield hydrophilic materials, which can be used as wound dressings or in cosmetic preparations. For example, U.S. Pat. No. 5,156,601 discloses a dressing, which includes a tacky gel of polyurethane and a poly (N-vinyl) lactam such as PVP. U.S. Pat. No. 5,420,197 describes hydrophilic gels formed by poly (N-vinyl) lactams, such as PVP, and chitosan. U.S. Pat. No. 6,121,375 disclose hydrophilic gel-like materials of PVP and polyaldehyde. Other references of general background interest include U.S. Pat. No. 5,206,322. All these materials are gel-like and non-biodegradable.

Although some of these hydrophilic materials can be used for wound dressings and other surgical and cosmetic applications, many hydrophilic materials known in the arts are hydrophilic gels that are non-biodegradable, and most of them are reversible.

It has also been known to make nonwoven fibrous-porous material on the base of a blend of poly (N-vinyl) pyrrolidone (PVP) and cellulose diacetate in component weight ratio of 1:(4-10) with high porosity and high moisture absorption prepared "in electrostatic field by continuous supply of an electrically charged polymeric solution through a nozzle" (Pat. RU No. 2111300). But this material is nonbiodegradable.

There is also known, Pat. RU No. 2031661, a microfibrous wound-healing remedy used for first and outdoors aid, prepared by the electrohydrodynamic method. The remedy comprises a composition of poly-d.l-lactide, poly (N-vinyl) pyrrolidone and a powdered sorptive material like polysaccharides networks, polyacrylates, cellulose esters or polyvinyl alcohol derivatives. The material could absorb 5-8 g/g water or blood; exhibited haemostatic abilities within 40 seconds and moderate wound healing effects. But introduction of nondegradable or slow degradable components such as polyvinyl alcohol derivatives into this material significantly decreased its biodegradation ability and limited its use for external application.

There is also known, Pat. RU No. 2120306, a totally biodegradable two layer dressing for wounds and burns consisting of a baking thin film layer (25-30 mkm) prepared from copoly (lactide-caprolactone) or copoly (lactide-glycolide) with a lactide/caprolactone or lactide/glycolide ratio of at most 50% w and a wound facing microfiber absorbent layer comprising a polylactide and poly (N-vinyl) pyrrolidone blend with a ratio of polylactide/poly (N-vinyl) pyrrolidone from 90/10 to 70/30 w/w. The microfiber absorbent layer is deposited on the film by the electrohydrodynamic method. The facing microfiber layer may also contain antiseptic, analgesic drugs and proteolysis ferments. The dressings described can absorb water and any biological liquids, including blood, at most 12 g/g and biodegrade within 12-36 days. However the vapor penetration of such dressings is at most 3.1 mg/cm$^2$ hour which precludes their use as dressings for wounds and burns that exhibit intensive "breathing", for example, large external fresh burns, bleeding wounds or different kinds of external injuries. Furthermore these dressings have poorly controllable time of degradation, which limits their application in the treatment of wounds and/or burns, and especially in the treatment of internal wounds. Better control over the degradation time is desirable.

There is also known a microfiber biodegradable polylactide web prepared by the electrospinning method from a polymer solution. The polymer concentration is 4-6% w. The voltage is 33-60 kV; the average fiber diameter is about 1 μm (See the article in Proceeding of the ACS, PMSE, p. 115, Mar. 26-30, 2000). But there is no evidence of any hydrophilic or bioactive properties of such a web. According to the article a solution of polylactide in dichloromethane was placed in a syringe. The syringe was positioned with its needle pointing down, The piston of the syringe was moved down with a controlled velocity by a motor. The negative pole was set at the metal capillary of the syringe and the positive pole on the substrate bearing. Paper was used as a substrate.

SUMMARY OF THE INVENTION

Some embodiments of the invention provide dressings, implants, dermatological compatible compositions and drug carrier compositions which include totally biodegradable non-gel materials having water, blood and other biological liquids absorption ability and possessing biological active properties like haemostatic and wound healing acceleration abilities, which are irreversible, retain their contour and shape when wet, and do not exhibit any swelling.

Some embodiments provide totally biodegradable microfiber absorbents on the base of blends of synthetic biodegradable polyesters and poly (N-vinyl) lactams. These materials can be used in a variety of products such as cavity dressings, drug delivery patches, face masks, implants, drug carriers, wound and burn dressings with predictable biodegradation times and controlled absorption of biological liquids including blood, and with variable vapor penetration and controlled drug release for wounds and burns.

Some embodiments provide a method of the totally biodegradable microfiber absorbent preparation.

Some embodiments of the invention provide totally biodegradable microfiber absorbents which can be used for or incorporated into dressing compositions, dermatologicaly compatible compositions, wound packing, wound dressings, burn dressings, living cells like keratinocytes and/or fibroblasts transplants, drug delivery dressings, cosmetic masks, cosmetic wrap dressings, drug carrier compositions. The absorbents may incorporate (e.g. be soaked in) protein containing drug (e.g. insulin) and other drugs. The absorbents of the invention include a blend of synthetic biodegradable polyester and a polymer selected from a group of poly (N-vinyl)-lactams, preferably poly (N-vinyl)-pyrrolidone.

The synthetic biodegradable polyesters useful in preparing the absorbents of the invention include, but are not limited to, homopolymers of L (−), D (+), d, l-lactide, glycolide, caprolactone, p-dioxanon and/or mixtures thereof, copolymers of L (−), D (+), d, l-lactide and glycolide, or caprolactone, or p-dioxanon, or polyoxyethylene glycols, and/or mixtures thereof, or copolymers of glycolide and caprolactone, or p-dioxanon. and/or mixture thereof.

The poly (N-vinyl) lactams useful in preparing the absorbents of the invention include, but are not limited to, homopolymers, copolymers of N-vinyl lactams such as N-vinylpyrrolidone, N-vinylbutyrolactam, N-vinylcaprolactam, and the like, as well as the foregoing prepared with minor amounts, for example, up to about 20 weight percent, of one or more of other vinyl monomers that are capable to copolymerize with the N-vinyl lactams like acrylic monomers or others. Of the poly (N-vinyl) lactam homopolymers, the poly (N-vinyl) pyrrolidone (PVP) homopolymers are preferred. A variety of poly (N-vinyl) pyrrolidones are commercially available.

The absorbent is prepared by the electrohydrodynamic processing of a blend (a melt or a solution) of poly (N-vinyl) lactam and biodegradable polyester. In one embodiment, the blend is a solution at a polyester/poly (N-vinyl) lactam ratio from about 99/1 to about 1/99 w/w, preferably from about 98/2 to about 50/50 w/w.

The present invention provides totally biodegradable absorbents which are capable of absorbing at least 20 w/w in water or blood without swelling, are irreversible and mechanically strong, have predictable biodegradation times, are capable of controlled medication delivery to the body, have a variable water vapor penetration. The materials of the present invention have the unexpected properties such as proper haemostatic properties, enhancing the healing of wounds, especially chronic wounds (e.g., diabetic wounds), ulcers, and proper antiseptics abilities. The dressing compositions of the present invention have the advantage of self-adhesion to the wet skin with easy peelability.

Totally biodegradable absorbents may include at least one additional ingredient, which may be releasable from the absorbent. Preferably, the releasable ingredients are bioeffecting or body-treating substances including various low molecular weight or polymeric drugs for internal or external delivery to the body exactly where desired. Such absorbents may also be used as a transplantable solid support or scaffold for living cells, such as keratinocytes or fibroblasts, growing and applied as a living cell transplant for burns and wounds.

The totally biodegradable hydrophilic nonwoven microfiber absorbents can be prepared by the electrohydrodynamic spinning from a polymer blend solution using 20-120 kV at a gap distance 15-40 cm, preferably 20-40 kV. The initial solution contains a blend of a biodegradable polymer and a poly (N-vinyl) lactam and may also contain different medications for immobilization of the material. It was unexpectedly discovered that by this method the material of the invention could be prepared.

Other benefits will be identified in the following description. The description is not in any way intended to limit the scope of the present invention, but rather only to provide a working example of the preferred embodiments. The scope of the present invention will be pointed out in the appended claims.

DETAILED DESCRIPTION

Figure 1:
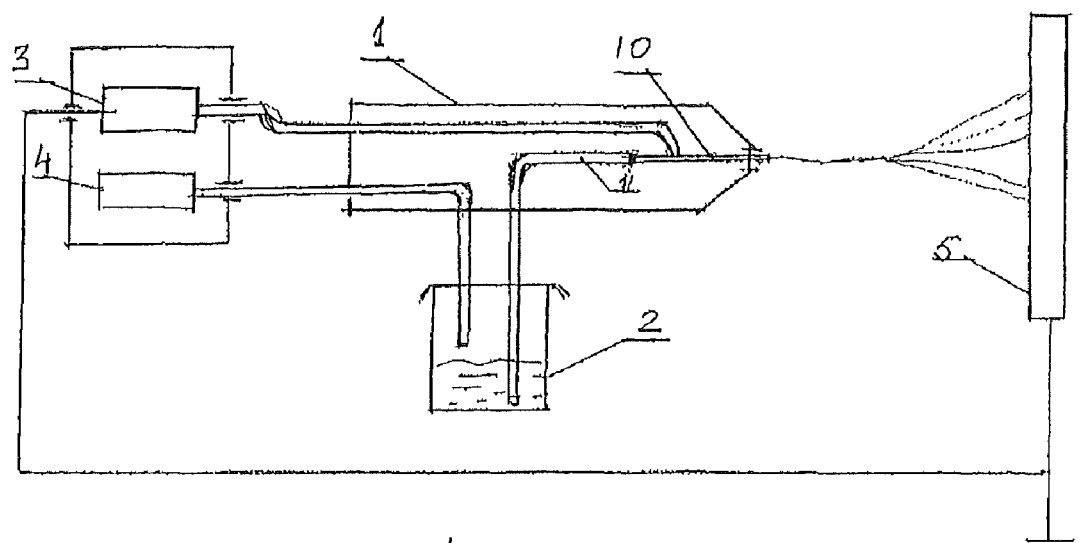
FIG. 1 is a schematic representation of a basic part of an electrohydrodynamic spinning apparatus, which was used to prepare a biodegradable absorbent in one embodiment. The device contains housing 1, container 2 for a polymer blend solution, power source 3 having one pole connected to a metal capillary electrode 10. The other pole is grounded. Compressor 4 provides compressed air into container 2. The compressed air forces the solution out of container 2 and into connecting tube 11, which conducts the solution into capillary electrode 10. The solution emerges from the electrode 10 as a jet flying towards the rotating drum 5. The electrostatic field generated by source 3 in the area between electrode 10 and drum 5 pulls out the solution stream into a thin thread. The solvent evaporates, and the thread becomes a solid fiber. These fibers are deposited on the surface of drum 5. Drum 5 can be replace with a stationary (non-moving) substrate.

Some embodiments of the invention provide a totally biodegradable hydrophilic nonwoven microfiber absorbents, impermeable to microbes, with variable degradation times and controlled vapor penetration for use in dressing, dressing compositions, drug carrier compositions, wound packing, wound dressings, burn dressings, including first aid dressings, drug delivery dressings, cosmetic mask dressings, cosmetic wrap dressings, cavity dressings for both internal and external applications. Cosmetic applications include skin rejuvenation and wrinkle removal. The absorbent of the invention includes a two-component blend. One component is a synthetic biodegradable polyester with different times of biodegradation selected from a group including, but not limited to, homopolymers or copolymers of L (−), D (+), d, l-lactide with glycolide, or caprolactone, or p-dioxanon, and/or mixtures thereof, or homopolymers or copolymers of caprolactone with L (−), or D (+), or d, l-lactide, or glycolide, or p-dioxanon and/or mixtures thereof, and copolymers of L (−), or D (+), or d, l-lactide, or caprolactone, or p-dioxanon with polyoxyethylene glycols (PEG) and/or mixtures thereof, or homopolymers or copolymers of p-dioxanon. The other component is a poly (N-vinyl) lactam selected from a group including, but not limited to, homopolymers, copolymers of N-vinyl lactams such as N-vinylpyrrolidone, N-vinylbutyrolactam, N-vinylcaprolactam, and the like, as well as the foregoing prepared with minor amounts, for example, up to about 15-20 weight percent, of one or more of other vinyl monomers copolymerizable with the N-vinyl lactams such as acrylic acid, acryl amides or hydroxyalkylacrylates. Of the poly (N-vinyl) lactam homopolymers, the poly (N-vinyl) pyrrolidone (PVP) homopolymers are preferred. A variety of poly (N-vinyl) pyrrolidones are commercially available.

To prepare a material with controlled biodegradation times, the ratio of polyester/poly (N-vinyl) lactam is used in the range from about 99/1 to about 1/99, preferably from about 98/2 to about 50/50 w/w for polylactide, or co (polylactide-glycolide) with a lactide/glycolide ratio from about 99/1 to about 50/50. Preferably, the poly (N-vinyl) pyrrolidone is used. Preferably, the molecular weights of the two components are in the range from $3 \times 10^4$ to $50 \times 10^4$ Dalton for polyester and from $0.5 \times 10^4$ to $4 \times 10^4$ Dalton for poly (N-vinyl) pyrrolidone. The biodegradable polyester component may contain caprolactone homopolymers and/or caprolactone copolymers with lactide (or glycolide) with a caprolactone/lactide (or glycolide) ratio from about 1/90 to about 99/1 w/w and with the molecular weights at least $15 \times 10^4$ Dalton for the polyester component and the polyester/poly (N-vinyl) pyrrolidone ratio from about 90/10 to about 50/50 w/w. The biodegradable polyester component may contain copolymers of glycolide (or lactide) and p-dioxanon with a glycolide (or lactide)/p-dioxanon ratio from about 50/50 to about 1/99 w/w.

For biodegradation time control, a low molecular weight polylactide or its copolymers with glycolide may be included into the blend in the amount of at least 5-10% w. The lactide/glycolide ratio is preferably 50/50 w/w. The molecular weights of these compounds are at least from $2 \times 10^3$ to $10 \times 10^3$ Dalton. Various low molecular weight or polymeric linear or branched alcohols such as mannitol, sorbitol, etc. or polyoxyethylene glycols (PEG) of different molecular weights, respectively, may be included into the blend in the amount of at least 5-10% w.

The totally biodegradable, hydrophilic unwoven absorbent consists of microfibers at most 0.1-5 μm is irreversible with non-leachable poly (N-vinyl) lactam. The material is capable of unswelling absorption at least 20 w/w in water or blood and/or other biological liquids with high absorption rates without changing the contour or shape of the device. The material is capable of delivering medicaments externally or internally to the body exactly where desired. The material of the present invention has by itself unexpected properties such as a haemostatic property and antiseptics property. The material enhances the healing of wounds, especially chronic wounds (e.g., diabetic wounds) and ulcers and may be applied without any additional medications. The material and its degradation products are biocompatible and don't induce any tissues immune response. The products based on the materials of the present invention have a good mechanical strength and preserve their shape under wet conditions. They can be sterilized by X-ray radiation. Other advantages obtained in some embodiments include softness and compliance with skin surfaces, and self-adhesion to the wet skin but with easy peelability and a variable "breathability".

To obtain a totally biodegradable, hydrophilic unwoven absorbent, the electrohydrodynamic method for solution spinning can be applied. The method involves spraying the solution of a polymer blend through a capillary nozzle onto a substrate. More particularly, the method consists in providing a stream of compressed air or some other gas through a capillary nozzle, and continuously introducing into the air stream a solution of a blend of a biodegradable polyester and poly (N-vinyl) pyrrolidone or other poly (N-vinyl) lactams in a solvent (e.g. dichloromethane or mixture of ethyl acetate and a lower alcohol. An exemplary concentration of the polymer in the solution is 1-40% w. The voltage between the nozzle and the substrate can be 20-120 kV, preferably 20-40 kV. The negative pole is set at the metal capillary of the nozzle. The substrate is grounded. The gap between the nozzle and the substrate is 15-40 cm. Depending on the voltage, gap value and polymer in the solution concentration, materials of a controlled density and microfiber diameters from 0.1-5 μm can be prepared. After the completion of the process the microfiber unwoven material is removed from the substrate, cut into pieces (for example, squares) and vacuum dried. A finished product is packed and sterilized by γ-radiation by conventional techniques.

The substrate can be either a static surface or a rotating drum as described in Russian patent RU 2121036 (20 Oct. 1998).

Figure 2:
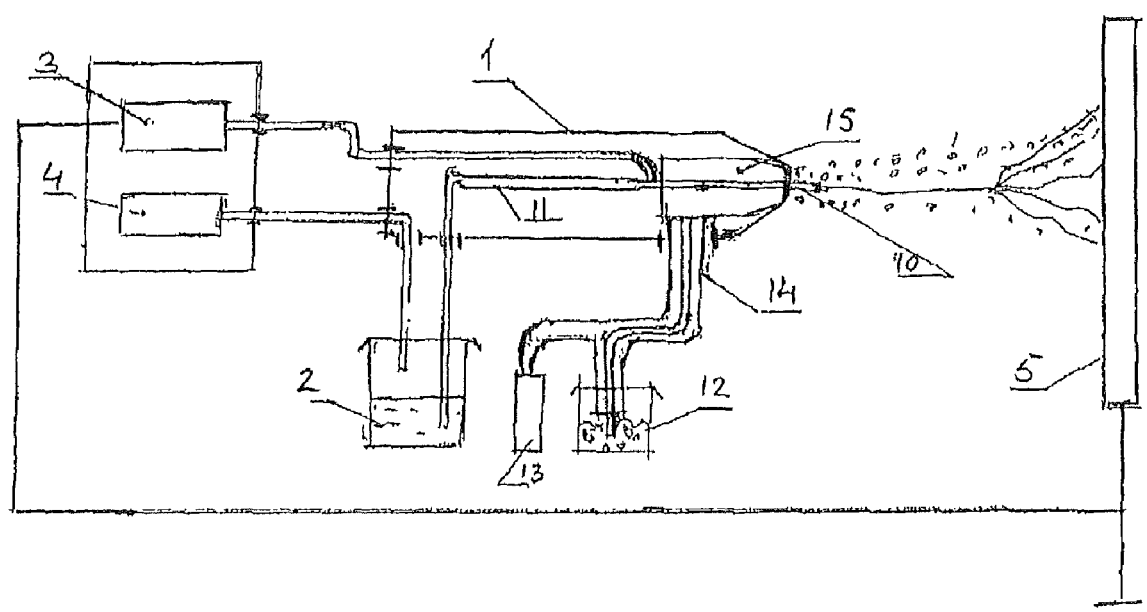
FIG. 2 is a schematic representation of a basic part of modified electrohydrodynamic spinning apparatus, which was used to immobilization for "dry" fine powder drugs including insoluble drugs into a biodegradable absorbent. The device as shown in FIG. 1 is modified by addition of a container 12 for a dry drug powder and of a microcompressor 13. Compressor 13 provides compressed air into container 12. The compressed air forces the powder out of container 12 and into connecting tube 14, which conducts the powder into a ring channel 15 surrounding a capillary electrode 10. The powder is sprayed towards the grounded surface of the rotating drum 5 and deposited simultaneously with the polymer microfibers or on the surface of a previously prepared microfiber mat.

FIG. 1 shows a schematic representation of a basic part of an apparatus of electrohydrodynamic spinning which was used for biodegradable absorbent of the invention preparation. The device contains housing 1, container 2 for polymer blend solution used for spinning, power source 3 connected to metal capillary electrode by one pole with the second pole setting grounded, compressor 4 connected with the container 2. The solution of a blend of a biodegradable polymer and poly (N-vinyl) lactam in a solvent is providing by a stream of compressed air from compressor 4 through a capillary nozzle with high voltage imposed from the source 3. A polymer solution jet flowing out of the capillary nozzle in the stream of compressed air under the action of electrostatic field forces is drawing off into at least one ultra thin fiber that is deposited on a grounded substrate surface that can be a rotating drum 5 or non-moving substrate. For apparatus productivity increase the device can be supplied with an additional compressed air source 13 comprising a ring channel 15 surrounding a capillary electrode 10 (FIG. 2).

Materials with a different degree of "breathability" can be obtained through: 1) selection of the microfiber thickness and packing density; 2) electrohydrodynamic microfiber deposition on at least 5-10 μm thick polymeric films of the appropriate breathability. These films can be prepared from biodegradable polymers and copolymers like polylactide, or poly (lactide-co-glycolide) with a lactide/glycolide ratio from about 1/99 to about 99/1, or poly (lactide-co-caprolactone) with a lactide/caprolactone ratio from about 1/99 to about 99/1, polycaprolactone, poly-p-dioxanon or its copolymers with glycolide or lactide with a p-dioxanon/lactide or glycolide ratio from about 1/99 to about 99/1. These biodegradable films, which serve as backing films in such dressings, may be prepared by any conventional methods of polymer processing from either a polymer melt or a polymer solution. A backing film with variable vapor permeability (i.e. breathability) can also be prepared from a mixture of biodegradable polyesters listed above and other biocompatible polymers of various molecular weights like polyoxyethylene glycols in the amount of at least 15% w. The backing film may also improve the mechanical properties of the dressings.

The "breathability" can also be increased by increasing the gap between the nozzle and the substrate if the electrohydrodynamic method is used. The "breathability" is believed to decrease if a higher voltage is used between the nozzle and the substrate. These techniques (gap size and voltage) can be used with or without the backing film. More particularly, in some embodiments, no backing film is present. The absorbent material is formed by the electrohydrodynamic method on a substrate as described above. The substrate can be a rotating drum. After this electrohydrodynamic deposition, the absorbent article is removed from the substrate. The article can be used without any backing film. Non-drum substrates including non-moving substrates, can be used.

The absorbent of the invention may also include at least one additional ingredient, which may be releasable from the absorbent. Preferably, the releasable ingredients are bioeffecting or body-treating substances including different low molecular weight or polymeric drugs for internal or external delivery to the body exactly where desired. Particularly preferred as biologically-active additives are also antimicrobials such as tetracycline, neomycin, oxytetracycline, triclosan, sodium cefazolin, silver sulfadiazine, and also salicylates such as methylsalicylate and salicylic acid, nicotinates such as methyl nicotinate; capsaicin, benzocaine, alpha-hydroxy acids, vitamins and biostats and others, or antioncology active drugs like doxorubicin, toxol and others or insulin, or interferon, or others.

When the material is used for wound and burn healing acceleration, it may contain living human cells like keratinocytes or fibroblasts previously grown on the material as on the solid porous scaffold.

To provide a prolonged and controlled drug release to the surface of internal and/or external wounds or burns, the material may contain two or more microfiber layers. Different layers may have different compositions. Each layer includes the biodegradable polymer with or without poly (N-vinyl) lactam. Different layers may also have different ratios of biodegradable polymer/poly (N-vinyl) lactam or different biodegradable polymers. Different types of polymers and/or copolymers may be used that may have different molecular weights, contain different biocompatible functional groups such as hydroxyl, carboxyl and/or amino groups or contain different additives such as low or high molecular weight alcohols like sorbitol, mannitol, starch, polyoxyethylene glycols, etc. Each layer may include at least one additional bioactive ingredient which may be releasable from the absorbent and which may be immobilized into polymeric matrix as by the electrohydrodynamic method as by conventional methods such as wetting of the material by drug solution.

When the electrohydrodynamic method is used for drug immobilization into an absorbent, the drug can be dissolved in a polymeric blend solution and immobilized using the device shown in FIG. 1 or can be immobilized as dry fine particles by compressed air steam using the modified device shown in FIG. 2.

For drug delivery systems, the material of the present invention may contain drugs immobilized by the electrohydrodynamics or other methods and then ground into fine particles of a size less than 10 µm. These particles can be used for parenteral drug administration as a suspension in water, or for oral delivery after tableting the particles prepared by conventional compression methods. Tablets for oral drug delivery may also be prepared by conventional methods of tablet compression of the non-ground material with immobilized drugs. For drug carrier usage, the material may be prepared for example from the blend of polylactide and poly (N-vinyl) pyrrolidone, and polylactide molecular weights are at least $5 \times 10^4$ Dalton. The following examples are intended to illustrate but not limit the invention. The claim will serve to define the invention.

In the following examples the preparation of biodegradable absorbents is described, which absorbents can be used as wound and burn dressings, drug carriers and for cosmetic applications. These examples should not be viewed as limiting the scope of the invention. The claims will serve to define the invention.

Example 1

A Biodegradable Absorbent Utilizing Microfibres Containing Poly (Lactide-Co-Glycolide and/or Poly-N-Vinyl) Pyrrolidone with Variable "Breathing" Capabilities Materials:
Poly (d.l-lactide-co-glycolide) with a lactide/glycolide ratio 70/30 w/w and with an average molecular weight of 150000 Dal and Poly-d.l-lactide with an average molecular weight of 230000 Dal was synthesized by conventional ring-opening polymerization from d.l-lactide and glycolide that were purchased from Russian National Institute of Monomers (Tula, Russia). Poly-(N-vinyl) pyrrolidone with an average molecular weight of 30000 Dal was purchased from a Russian enterprise.
Methods.
1. Solution Preparation.
Poly (d.l-lactide-co-glycolide) (PLGA) was dissolved in ethyl acetate to make a 20% (w/w) solution with solution viscosity 1-2 poise (Solution A) or a 10% (w/w) solution with solution viscosity 0.5 poise (Solution B). Poly-(N-vinyl) pyrrolidone (PVP) was dissolved in ethanol making a 20% (w/w) solution and mixed with the PLGA solution in ethyl acetate at PVP/PLGA ratio of 20/80 (w/w) that was used for the electrohydrodynamic spinning.
2. Microfiber Material Preparation.
The PLGA/PVP solution was filtered to remove mechanical and gel-like impurities and was placed into a container 2 (FIG. 1) and spun into wound dressing materials in the form of microfiber mats, which were collected on the surface of a rotating drum 5 or on a film positioned on the surface of a rotating drum 5 that is used as a substrate. After the completion of the process, the microfiber unwoven material was cut into squares and vacuum dried to remove the solvent residue. The finished product was packed into a polyethylene laminated aluminum foil and sterilized by 2.5 Mrad γ-radiation using a conventional procedure.
3. Measurements of Microfiber Material Properties.
To measure the degree of absorbency, 2 cm² strips (0.5×4 cm) of the microfiber mat were cut and weighed (dry weight or DW), The end of the narrow side (0.5 cm side) of the strip was immersed in water or blood and soaked for 10-15 min. The liquid was drained and the strip was weighed (wet weight or WW). The content of water or blood absorbed by the material calculated using the equation:

$$\text{Water/blood absorbed content} = (WW - DW)/DW, g/g$$

Data on biodegradation times and haemostatic abilities of the material were obtained from in vivo experiments.
Sample 1.
Solution A: (PVP/PLGA in ethyl acetate, 20% PLGA) was spun by the electrohydrodynamic method with 30 kV at 25 cm gap distance L (FIG. 1) for 1 hour. The microfiber thickness was around 1.5-2 µm with a surface density (a coating level) ~5 mg/cm².
Sample 2.
Solution B: (PVP/PLGA in ethyl acetate, 10% PLGA) was spun by the electrohydrodynamic method with 30 kV at 25 cm gap distance L (FIG. 1) for 1 hour. The microfiber thickness was around 0.5-1 µm with a surface density (a coating level) ~2.5 mg/cm².
Sample 3.
Solution A: (PVP/PLGA in ethyl acetate, 20% PLGA) was spun by the electrohydrodynamic method with 40 kV at 25 cm gap distance L (FIG. 1) for 1 hour. The microfiber thickness was around 1-1.5 µm with a surface density (a coating level) ~5 mg/cm².

Sample 4.

Solution A: (PVP/PLGA in ethyl acetate, 20% PLGA) was spun the electrohydrodynamic method with 30 kV at 40 cm gap distance L (FIG. 1) for 1 hour. The microfiber thickness was around 1.5-2 µm with a microfiber surface density (a coating level) ~3 mg/cm².

Sample 5.

Solution A: (PVP/PLGA in ethyl acetate, 20% PLGA) was spun by the electrohydrodynamic method with 30 kV at 25 cm gap distance L (FIG. 1). Drum 5 was covered by a poly (d.l-lactide) film (backing film) having a thickness of 8-10 µm. The film was formed from 10% w solution of Poly-d.l-lactide in methylene chloride. The microfibers were deposited on the film. The fiber size was around 1.5-2 µm with a microfiber surface density (a coating level) ~5 mg/cm².

Test results for the materials in Samples 1-5 are summarized in Table 1.

TABLE 1

Physical-chemical and biomedical properties of biodegradable absorbents.

| Sample # | Moisture vapor penetration, Mg/cm² hour | Water/Blood absorbance, g/g | Times of biodegradation in vivo*, days | Microbial penetration |
|---|---|---|---|---|
| 1 | 5-7 | 15-20/19-20 | 3-5 | Non penetrable |
| 2 | 2-3.5 | 10-15/14-18 | 3-5 | Non penetrable |
| 3 | 5-7 | 12-15/16-18 | 3-5 | Non penetrable |
| 4 | 7-8 | 12-15/16-18 | 3-5 | Non penetrable |
| 5 | 2-2.7 | 15-20/18-20 | 7-8 | Non penetrable |

*Visual observation of in vivo degradation of equal square pieces of the material on the surface of fresh clean wounds formed on rat skin.

Example 2

Preparation of Fiber and/or Biodegradable Absorbent with Additional Therapeutic Performance Sample 1.

Silver sulfadiazine was dissolved under slight heating in ethanol to form a 5% solution and then added to the PLGA/PVP solution described above to yield a 1% silver sulfadiazine concentration in the final material. The solution was spun by the electrohydrodynamic method with 30 kV at 25 cm gap distance L (FIG. 1) for 1 hour. The microfiber thickness was around 1.5-2 µm with a surface density (a coating level) ~5 mg/cm².

Sample 2.

Silver sulfadiazine in the form of fine particles was placed into container 12 (FIG. 2) and immobilized using a compressed air stream (~0.5 atm) onto the surface of a just prepared absorbent deposited on a surface of a rotating drum using 30 kV at a gap distance 25 cm.

The invention is not limited by the embodiments described above, For example, in the electrohydrodynamic method, an alternating electric field can be used. Also, solutions can be replaced by melts. Other embodiments are within the scope of the invention as defined by the appended claims.

We claim:

1. A biodegradable structure comprising an electrohydrodynamic processed mixture containing:
   (a) a solvent;
   (b) poly-(N-vinyl)pyrrolidone; and
   (c) a biodegradable polyester which includes a caprolactone or a dioxanon of a molecular mass at least 150000 Dalton, with a component ratio of the poly-(N-vinyl) pyrrolidone to the caprolactone or diaxanon by weight being about 10:90 to about 50:50.

2. The biodegradable structure of claim 1, wherein said mixture further comprises one or more low molecular weight biodegradable polyesters with hydroxyl, carboxyl or amino-terminal groups, or one or more polyoxyethylene glycols, or one or more low molecular weight alcohols selected from the group containing alcohols, including alcohols of natural origin.

3. The biodegradable structure of claim 1, further comprising one or more of living cells, proteins, peptides, antibiotic compounds, bacteriocidal compounds, fungicidal compounds, bacteriostatic compounds, analgesic compounds, and trombogenic compounds.

4. The biodegradable structure of claim 1, wherein the mixture further comprises one or more biodegradable polyesters with hydroxyl, carboxyl or amino-terminal groups, and/or one or more polyoxyethylene glycols, or one or more alcohols.

5. The biodegradable structure of claim 1, wherein the mixture further comprises a compound selected from the group consisting of polyoxyethylene glycol, salicylates, methylsalicylate, salicylic acid, and nicotenates.

6. The biodegradable structure of claim 1, wherein the mixture further comprises an antimicrobial substance.

7. The biodegradable structure of claim 1, wherein the mixture further comprises a compound selected from the group consisting of tetracycline, neomycin, oxytetracycline, triclosan, sodium cefazolin, doxorubicin, toxol, insulin, and interferon.

8. The biodegradable structure of claim 1, further comprising one or more alpha hydroxy acids.

9. The biodegradable structure of claim 1, wherein the electrohydrodynamic process mixture is processed by an electrospinning technique.

10. The biodegradable structure of claim 1, wherein the mixture further comprises at least one copolymer that includes a polyether or a polyoxyethylene glycol and a polymer of a lactides, a dioxanon, a caprolactone or a glycolide.

11. A method for preparing a biodegradable microfiber absorbent, the method comprising electrohydrodynamic processing of a mixture containing:
   (a) a solvent;
   (b) poly-(N-vinyl)pyrrolidone; and
   (c) a biodegradable polyester which includes a caprolactone or a dioxanon of a molecular mass at least 150000 Dalton, with a component ratio of the poly-(N-vinyl) pyrrolidone to the caprolactone or diaxanon by weight being about 10:90 to about 50:50.

12. The method of claim 11, wherein said mixture further comprises one or more low molecular weight biodegradable polyesters with hydroxyl, carboxyl or amino-terminal groups, or one or more polyoxyethylene glycols, or one or more low molecular weight alcohols selected from the group containing alcohols, including alcohols of natural origin.

13. The method of claim 11, further comprising incorporating into the absorbent at least one therapeutic performance enhancing additive comprising one or more of living cells, proteins, peptides, antibiotic compounds, bacteriocidal compounds, fungicidal compounds, bacteriostatic compounds, analgesic compounds, and trombogenic compounds.

14. The method of claim 11, wherein the electrohydrodynamic processing comprises emitting a flow of said mixture into an area in which said mixture flies in an electrical field towards a substrate; and the method further comprises emitting a flow of dry particles into said area and the dry particles being deposited over said substrate.

15. The method of claim 14, wherein the flow of dry particles and the flow of said mixture are emitted into said area in overlapping periods of time.

16. The method of claim 11, wherein the mixture further comprises at least one therapeutic performance-enhancing additive.

17. The method of claim 11, wherein the mixture has an intrinsic viscosity from about 0.1 to about 10 poise.

18. The method of claim 11, wherein the mixture further comprises one or more biodegradable polyesters with hydroxyl, carboxyl or amino-terminal groups, and/or one or more polyoxyethylene glycols, or one or more alcohols.

19. The method of claim 11, wherein the mixture further comprises a compound selected from the group consisting of polyoxyethylene glycol, salicylates, methylsalicylate, salicylic acid, and nicotenates.

20. The method of claim 11, wherein the mixture further comprises an antimicrobial substance.

21. The method of claim 11, wherein the mixture further comprises a compound selected from the group consisting of tetracycline, neomycin, oxytetracycline, triclosan, sodium cefazolin, doxorubicin, toxol, insulin, and interferon.

22. The method of claim 11, further comprising including into the mixture one or more alpha hydroxy acids.

23. The method of claim 11, wherein the mixture further comprises at least one copolymer that includes a polyether or a polyoxyethylene glycol and a polymer of a lactides, a dioxanon, a caprolactone or a glycolide.

* * * * *